United States Patent
Putz et al.

(10) Patent No.: US 6,629,990 B2
(45) Date of Patent: Oct. 7, 2003

(54) HEAT-REMOVAL METHOD AND APPARATUS FOR TREATMENT OF MOVEMENT DISORDER EPISODES

(75) Inventors: David A. Putz, Franksville, WI (US); John Ziobro, Delafield, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 0 days.

(21) Appl. No.: 09/904,802

(22) Filed: Jul. 13, 2001

(65) Prior Publication Data

US 2003/0014097 A1 Jan. 16, 2003

(51) Int. Cl.[7] .................................................. A61F 7/12
(52) U.S. Cl. ............................ 607/113; 607/96; 607/99
(58) Field of Search .............................. 607/96, 98, 99, 607/113; 606/20, 21, 27; 600/544, 545

(56) References Cited

U.S. PATENT DOCUMENTS

| | | | |
|---|---|---|---|
| 4,903,702 A | * 2/1990 | Putz | ........................... 600/377 |
| 5,197,466 A | 3/1993 | Marchosky et al. | |
| 5,215,086 A | 6/1993 | Terry, Jr. et al. | |
| 5,261,399 A | 11/1993 | Klatz et al. | |
| 5,843,093 A | * 12/1998 | Howard, III | ................ 600/372 |
| 5,913,885 A | 6/1999 | Klatz et al. | |
| 5,995,868 A | 11/1999 | Dorfmeister et al. | |
| 6,006,124 A | 12/1999 | Fischell et al. | |
| 6,126,680 A | 10/2000 | Wass | |
| 6,128,527 A | 10/2000 | Howard, III et al. | |
| 6,248,126 B1 | 6/2001 | Lesser et al. | |

* cited by examiner

Primary Examiner—Roy D. Gibson
(74) Attorney, Agent, or Firm—Jansson, Shupe & Munger, Ltd.

(57) ABSTRACT

Heat-removal method and apparatus for treatment of movement disorder episodes; more specifically, a device and method for intracranially suppressing movement disorder episodes upon the detection of physiological symptoms. The device includes a temperature-contact implanted at a targeted portion in the brain which is determined to be associated with such episodes and connection to an implanted heat-transfer operator, typically a Peltier cooler or a thermal-electric cooler. Heat transfer from the temperature-contact to the heat-transfer operator cools the targeted portion and suppresses the movement disorder episode. Such heat transfer is performed upon the sensing of symptoms which normally preface episodes. The symptoms can be sensed intracranially by sensing-contacts, on the skin by a sensor or by a person or animal. Alternatively, heat removal (cooling) can be performed without sensing symptoms to prevent episodes when the patient is particularly sensitive to, or in danger from, episodes.

77 Claims, 6 Drawing Sheets

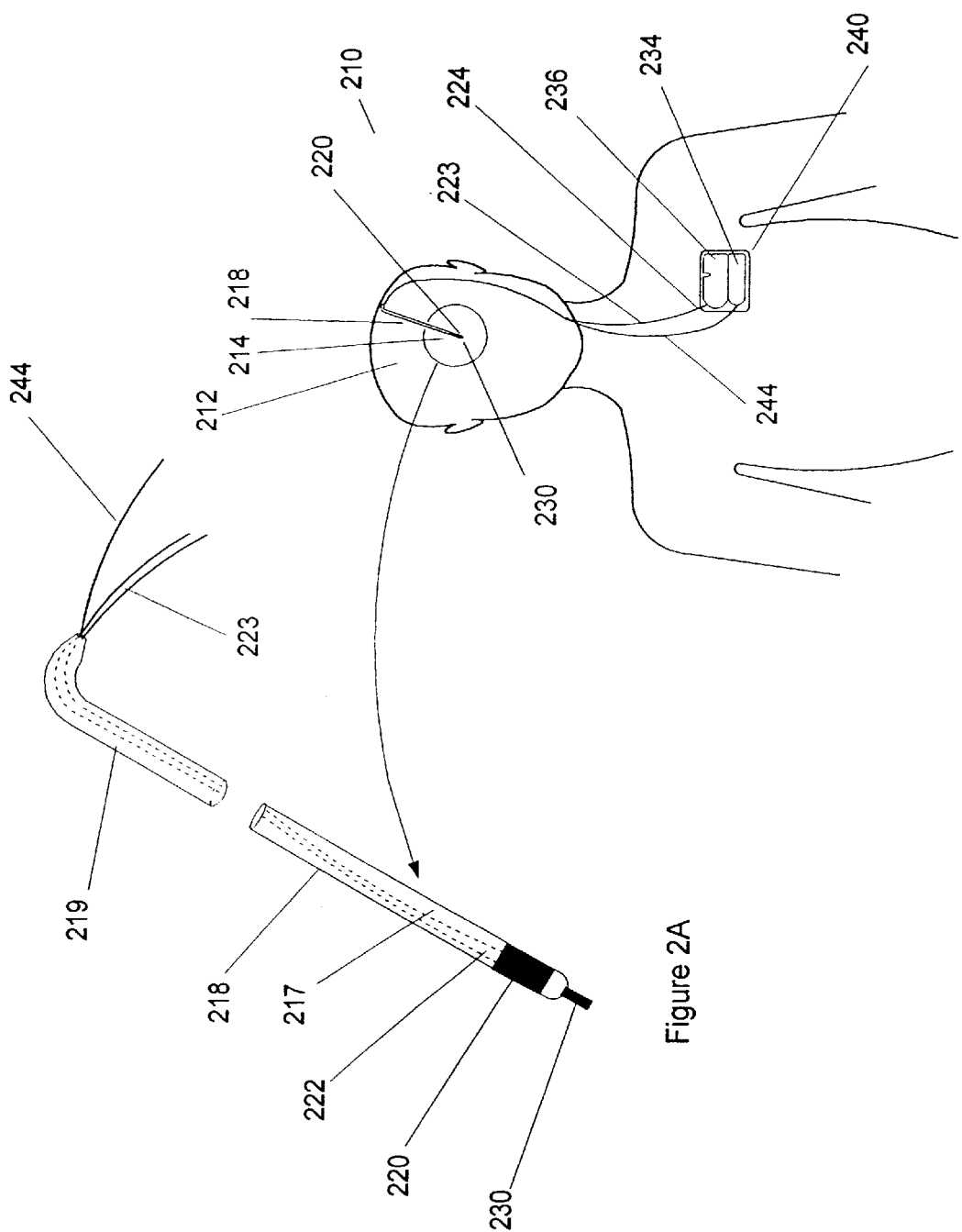

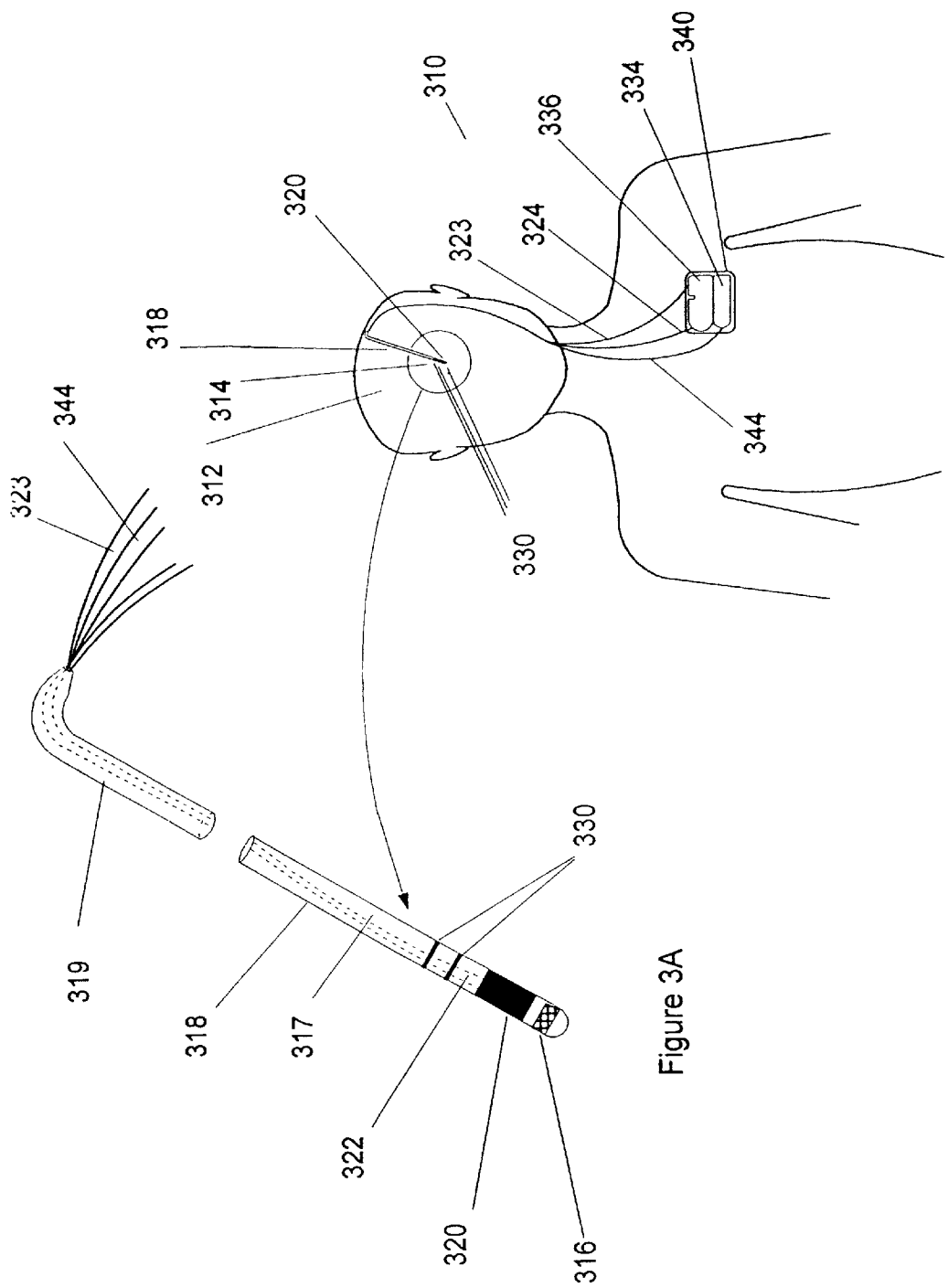

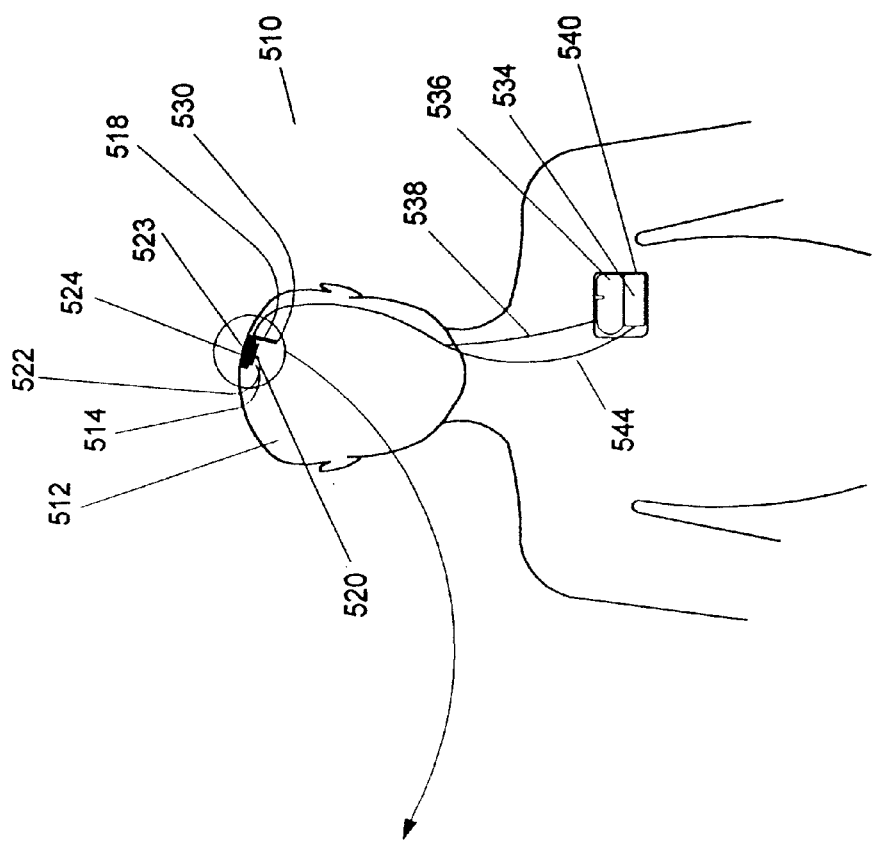
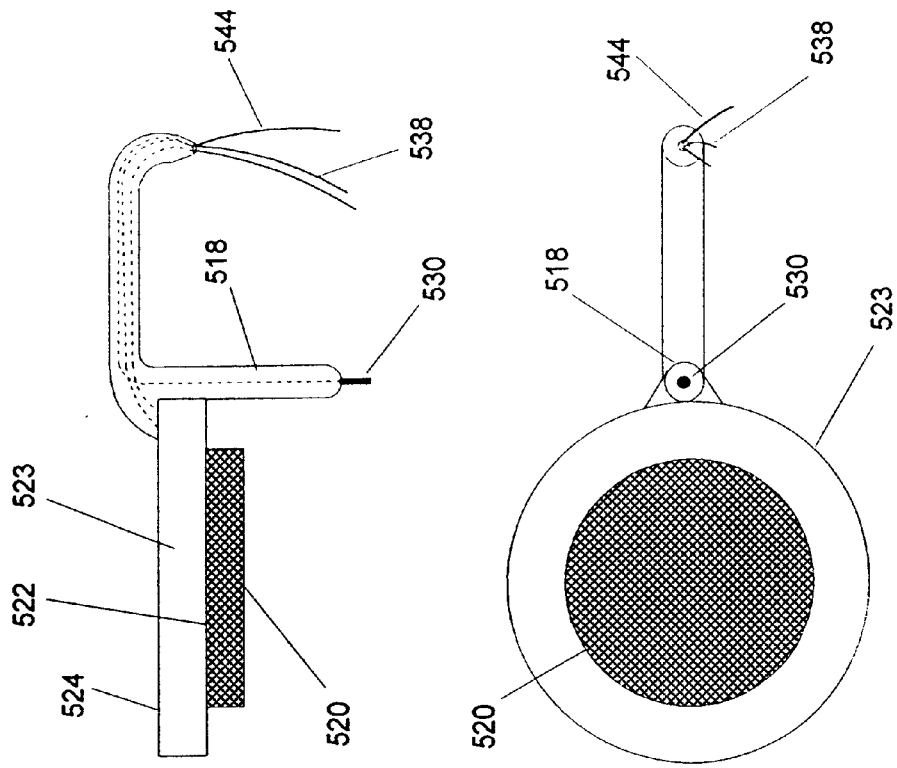
Figure 5
Figure 5B
Figure 5A

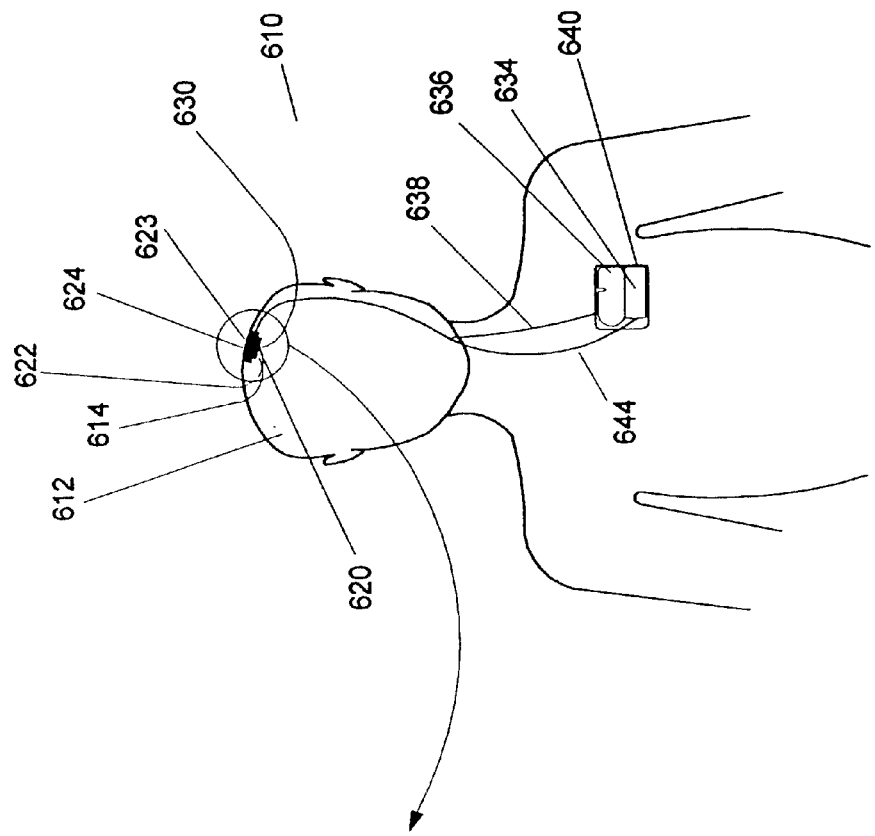
Figure 6
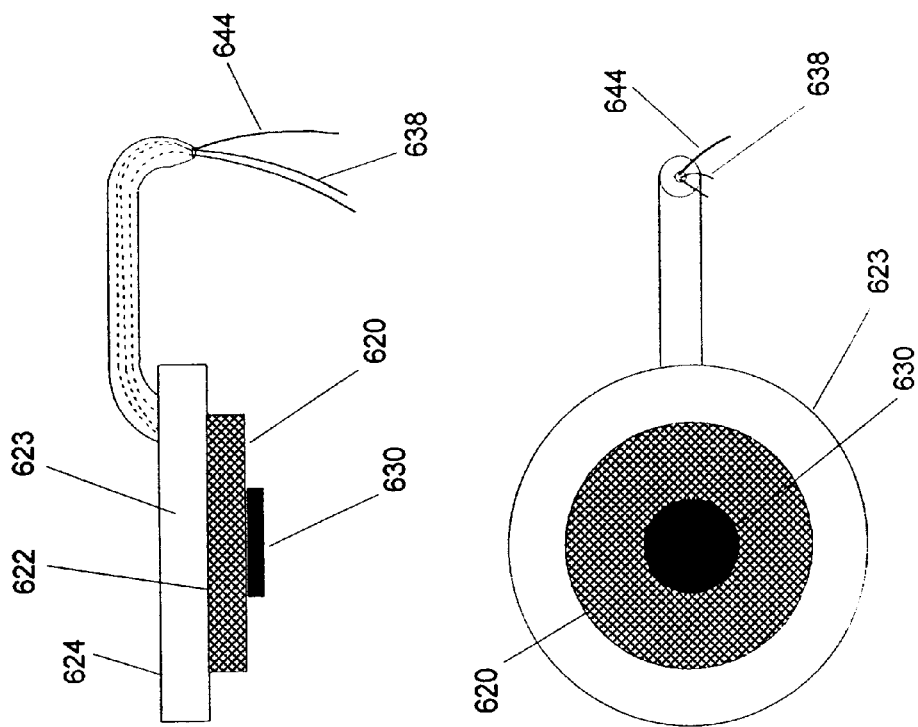
Figure 6B
Figure 6A

HEAT-REMOVAL METHOD AND APPARATUS FOR TREATMENT OF MOVEMENT DISORDER EPISODES

FIELD OF THE INVENTION

The invention relates generally to treatment of movement disorders and, more particularly, to intracranial treatment utilizing identification of an incipient movement disorder.

BACKGROUND OF THE INVENTION

Movement disorders such as epilepsy and Parkinson's disease have been estimated to affect some 1–2% of the developed world's population and up to 10% of people in underdeveloped countries. Currently, approximately 75% of those who suffer from movement disorders are responsive in some degree to drugs. However, undesirable side effects often prevent such treatment.

In addition, drug treatment often imposes a continual effect on brain cells and other tissues commonly resulting in the perpetual presence of side effects, while the movement disorder episodes, e.g., epileptic seizures, sought to be prevented occur much less frequently. Furthermore, patients often develop such high tolerances for the drugs administered that they are no longer effective at safe dosages. Therefore, there has been a need for movement disorder suppression which avoids the use of drugs.

Electrical stimulation has been utilized to treat some movement disorders. In the treatment of epilepsy, studies have been performed in which awake patients undergoing temporal lobe surgery underwent cortical stimulation. Such stimulation of the visual and hearing areas of the brain reproducibly caused the patients to experience visual and auditory phenomena. This discovery was made possible by the identification that certain brain subregions served specific functions, such as sight, hearing, touch and movement of the extremities and proved that direct electrical stimulation of the brain regions could cause partial reproduction or suppression of the functions.

As suggested by these results, it is known that certain types of treatment of specific portions of the brain are able to suppress certain unwanted behavior which results from movement disorders. This behavior may include seizures such as those suffered by epileptics. However, the studies faced a major problem in that there was an inability to precisely electrically stimulate very small volumes of the brain.

The advent of needle-shaped penetrating depth electrodes helped to overcome this obstacle faced by electrical stimulation. Depth electrodes can be placed within the brain tissue itself, enabling optimal surface contact with elements of the brain that are targeted for stimulation. This allowed for safe, chronic electrical stimulation of very small discrete volumes of brain.

There have been attempts to provide neurocybernetic prostheses for alleviating epilepsy and related disorders. U.S. Pat. No. 4,702,254 to Zabara discloses a prosthesis which comprises a miniature electronic integrated circuit with an output which augments appropriate brain neural discharge to control convulsions or seizures. The Zabara device uses neural spectral discrimination by tuning the electrical current of the prosthesis to the electrochemical properties of a specific group of inhibitory nerves that affect the reticular system of the brain. Certain electrical parameters of the prosthesis must be selected based on the electrochemical properties of the nerves desired to be activated. The patent teaches that the optimal site for the application of the prosthesis is on the vagus nerve.

While the electrical stimulation of brain tissue has been somewhat effective in the treatment of migraines, epilepsy and other neurological problems, patients often experience diminishing returns with such treatment. Furthermore, because each patient reacts differently to electrical stimulation, substantial time must be spent to determine the specific amplitude, frequency, pulse width, stimulation duration, etc. which may result in effective treatment. In addition, such parameters often require continual adjustment in order to remain effective.

In treatment, electrical stimulation has been used with the recording and analysis of electrical changes in brain activity to predict the occurrence of epileptic seizures. The time of onset of such seizures is often predictable by neural discharge monitoring, even when the exact causal nature of precipitating dysfunction is not understood. U.S. Pat. No. 5,995,868 to Dorfmeister discloses the use of electrodes to obtain signals representative of current brain activity and a signal processor for continuous monitoring and analysis of these electrical signals in order to identify important changes or the appearance of precursors predictive of an impending change. Dorfmeister mainly discusses the quick identification of the onset of a seizure; cooling a portion of the brain in response to such identification is mentioned, but he does not discuss how such cooling could be performed.

At the time of Dorfmeister, the treatment of various disorders of and injuries to the brain utilizing the transfer of heat away from (cooling) the brain was well known in the medical arts and was often performed using the external application of cold fluids, housed chemicals involved in endothermic reactions or other refrigerants. Other methods of cooling include the external cooling of blood which is recirculated through the body.

U.S. Pat. Nos. 4,750,493 and 4,920,963 to Brader are directed to a method for cooling the extracranial area during emergency care of cardiac arrest or extreme shock in order to induce vasoconstriction and intracranial hypothermia. These inventions are implemented by a topical cold pack or watertight shroud which cannot specifically cool a targeted portion in the brain. U.S. Pat. No. 5,383,854 to Safar et al. is directed to a cardiopulmonary bypass apparatus which is able to cool the blood. This device cannot specifically cool a target portion in the brain either.

U.S. Pat. No. 6,188,930 B1 to Carson is directed to a method for heating the hypothalamus which utilizes a device for cooling the surrounding body tissues. This device is not implanted, but is used temporarily during or preceding surgery. The patent discloses cooling through the circulation of a liquid or gas coolant through a catheter. Chronic cooling of a targeted portion in the brain is not disclosed.

U.S. Pat. No. 6,090,132 to Fox is directed to a method of inducing hypothermia in a mammal. This invention applies heat to the hypothalamus in order to effect a compensatory cooling response, thereby lowering body temperature. The patent discloses the direct application of heat to the hypothalamus for a temporary cooling effect. The patent does not disclose chronic treatment using an implanted device, nor the cooling of a specific portion.

U.S. Pat. No. 5,215,086 to Terry employs a neurostimulator to selectively apply electrical therapy to treat migraines. The neurostimulator delivers pulses of electricity of a specific pulse width and amplitude to the patient's vagus nerve in order to stimulate nerve fibers and either synchronize or desynchronize the EEG and control migraines.

U.S. Pat. Nos. 5,843,093 and 6,129,685 to Howard relate to the selective treatment of neurons within the brain with particular emphasis on the treatment of Parkinson's through pallidotomy and on the regulation of a patient's appetite through electrical discharges to the hypothalamus. Both of these patents disclose the inactivation of neurons through the use of a cryogenic device, though they do not teach what the cryogenic device could be or how it might be safely disposed within the brain.

Despite the Dorfmeister and Howard disclosures, it has not yet been possible, upon recognition of an incipient movement disorder, to effectively and immediately cool a localized area in the brain with an implanted device episode which can avoid undue risk or injury to the brain. An implanted device for thermal treatment of movement disorders episodes which addresses the problems of known treatments would be an important advance in the art.

OBJECTS OF THE INVENTION

It is an object of the invention to provide an implanted device for thermal treatment of movement disorders overcoming some of the problems and shortcomings of prior art devices for suppressing movement disorders.

Another object of the invention is to provide a method of suppressing movement disorder episodes in people immediately upon detection of an incipient episode.

Another object of the invention is to provide a method of suppressing movement disorder episodes through the implantation of a device which, after implantation, requires no further surgery for an extended period of time.

Another object of the invention is to provide a method of suppressing movement disorder episodes through the localized transfer of heat away from a targeted portion of the brain.

Another object of the invention is to provide a method of suppressing movement disorder episodes without the use of electrical stimulation of brain tissue.

Still another object of the invention is to provide a method of suppressing movement disorder episodes without the use of drugs.

Another object of the invention is to provide a method of suppressing movement disorder episodes which safely transfers heat from selected brain tissue without risk of damage to other brain tissue.

Another object of the invention is to provide a method of suppressing movement disorder episodes which safely transfer heat from selected brain tissue without affecting surrounding brain tissue.

Yet another object of the invention is to provide a method of suppressing movement disorder episodes which transfers heat from a selected volume of the brain in an energy efficient manner.

Still another object of the invention is to provide a method of suppressing movement disorder episodes after the detection of electrical, electrochemical, chemical, optical or blood flow changes in the brain.

How these and other objects are accomplished will become apparent from the following descriptions and drawings herein.

SUMMARY OF THE INVENTION

The implanted thermal transfer device for treatment of movement disorder episodes, and method of use thereof, are intended to prevent or suppress movement disorder episodes, such as epileptic seizures, through the transfer of heat away from a targeted portion in the brain that has been previously identified as being associated with movement disorder episodes in the patient. The invention solves the problems and overcomes the limitations of the prior art, while providing pioneering advances in the state of the art.

The preferred embodiment of the apparatus of this invention provides for the rapid transfer of heat away from (cooling of) a selected portion, or volume, in a patient's brain upon detection of a physiological symptom of an incipient movement disorder episode. This targeted portion of the brain may be a very small, point-like volume. Such physiological symptoms may be particular to the patient, and may evolve during the patient's lifetime. The transfer of heat automatically ceases upon the attainment of sufficient cooling at the targeted portion. Such sufficient cooling may be determined by the temperature at the targeted portion, the duration of the heat transfer which may be programmed in a controller, the subsidence of physiological symptoms or the presence of physiological evidence that the episode has been suppressed.

The preferred device comprises at least one temperature-contact positioned at a targeted portion in the brain. The temperature-contact is thermally coupled to the cold junction of a heat-transfer operator such that heat is compelled to flow from the temperature-contact into the cold junction to affect cooling at the targeted portion. The temperature-contact can be positioned adjacent to the targeted portion, or simply near the targeted portion, so that heat transfer by the temperature-contact effectively cools the targeted portion.

The preferred heat-transfer operator is a Peltier cooler or a thermal-electric cooler. Such heat-transfer operators pass electricity through junctions between dissimilar metals. The atoms of the dissimilar metals have a difference in energy levels which results in a step between energy levels at each of the metals' junctions. As electricity is passed through the metals, the electrons of the metal with the lower energy level pass the first step as they flow to the metal with the higher energy level. In order to pass this step and continue the circuit, the electrons must absorb heat energy which causes the metal at the first junction to cool. At the opposite junction, where electrons travel from a high energy level to a low energy level they give off energy which results in an increase in temperature at that junction.

In the context of this application, Peltier cooler refers to a system wherein pairs of dissimilar materials are joined at two junctions which are separated by a substantial length. For instance, for each pair the cold junction could be positioned in the brain and the hot junction could be positioned in the abdomen. The dissimilar materials may extend to each junction forming a circuit or loop. The dissimilar materials may also be separately connected to other conductors such that the circuit or loop is comprised of a cold junction of dissimilar first and second materials, a hot junction of dissimilar first and second materials, a conductor connecting the ends of the first material and a conductor connecting the ends of the second material.

Thermal-electric cooler refers to a system wherein the cold and hot junctions are not separated by a substantial length. For instance, the cold junction of the thermal-electric cooler may be positioned on the surface of the brain and the hot junction could be positioned on a surface in substantial conformity with the external surface of the skull. While in principle a single piece of semiconducting material can be used in a thermal-electric cooler, connection of multiple semiconducting materials in series is preferred to avoid the high current requirement of the single element.

As stated above, the Peltier cooler includes at least one circuit or loop of dissimilar materials, preferably semiconducting materials, which are connected at two junctions. The Peltier cooler is preferably implanted in the patient so that its cold junction is adjacent to the temperature-contact and its hot junction is located away from the brain, preferably in the torso. The hot junction is most preferably located adjacent to, and thermally coupled to, a titanium housing which acts to dissipate heat. The Peltier cooler circuit or loop which extends between the two junctions is electrically insulated and preferably implanted such that it travels from the cold junction at the temperature-contact, out of the skull, down the neck and into the torso.

In the preferred embodiment utilizing the Peltier cooler, the temperature-contact is preferably located on the distal end of a depth-electrode type probe which is implanted in the patient's brain. The cold junction of the Peltier cooler is connected to the temperature-contact in the brain. The Peltier circuit or loop extends out of the skull through the proximate end of the probe, down the neck and into the abdomen where the hot junction can transfer heat to another device, such as a titanium housing or other metal enclosure, or otherwise allow heat to safely dissipate into the body.

For the Peltier cooler, the preferred temperature-contact is a gold or platinum foil or collar which preferably encircles a portion of the distal end of the probe. The temperature-contact must be an extremely thermally conductive material which is harmless to the surrounding brain tissue.

In the alternative embodiment using a thermal-electric cooler, the temperature-contact is a gold or platinum foil or collar which has a surface which corresponds to the surface of the brain. The temperature-contact is preferably implanted in the patient adjacent to the skull.

The temperature-contact is connected, or thermally coupled, to the cold junction of the thermal-electric cooler. The temperature-contact is preferably located on the face of the cold-junction. A portion of the skull can be removed so that the temperature-contact can be placed adjacent to the brain and the skull with the thermal-electric cooler directly adjacent to the skull. The thermal-electric cooler can be positioned in the void created when a portion of the skull was removed such that an observer of the patient could not easily perceive the implanted device.

Whether utilizing a Peltier cooler or a thermal-electric cooler as a heat-transfer operator, the heat-transfer operator is electrically connected to an implanted power source which supplies a current through the heat-transfer operator to affect heat transfer. The power source operates efficiently by powering off the heat-transfer operator supply when heat transfer is not needed. When heat transfer is desired, the power source can be activated to supply a DC current to the heat-transfer operator which will, in turn, activate heat transfer from the targeted portion through the temperature-contact to the cold junction of the heat-transfer operator.

It is contemplated that the power source may be switched on or activated automatically or remotely by a person. The power source preferably provides power from an implanted battery which holds sufficient power so that once implanted, further operations to recharge the battery, or install a new battery, are not needed for an extended period of time, perhaps for as long as the life of the patient.

The power source is preferably implanted in the patient away from the brain, most preferably in the patient's torso. The power source can located within a titanium housing or other metal enclosure which may provide electrical grounding.

To allow for automatic activation of the heat-transfer operator, sensing-contacts are utilized to detect a physiological symptom of an incipient movement disorder episode. The sensing-contacts are preferably positioned in the brain at a location which has been determined to be a site at which symptoms of impending movement disorder episodes may be detected and measured. The physiological symptoms detected by the sensing-contact can be electrical, electrochemical, chemical, optical or blood flow changes within the brain or other symptoms.

Such electrical and electrochemical symptoms can be changes in the patient's EEG, changes in the patient's intracellular EEG or the like which are recognized as precursors of episodes. These electrical and electrochemical symptoms are often related to intracellular gate changes. Such electrochemical and chemical symptoms can be the presence or change in amount of certain biogenic chemicals present near the sensing-contact, particularly neurotransmitters such as amines, amine metabolites, ascorbic acid, amino acids and neuropeptides or dopamine, glutamate, aspartate, seratonin or the receptors, metabolites, precursors, agonists, antagonists or related enzymes of such chemicals or sodium, potassium or chloride ions or nitrous oxide.

The sensing-contacts may be micro sensing-contacts which have surfaces with diameters of about 25 microns. The sensing-contacts can also be macro sensing-contacts which are cylinder type collars with lengths of about 2.5 millimeters and diameters of about 1.1 millimeters. Sensing-contacts are preferably gold or platinum though, as is recognized in the art, any conductive corrosion-resistant and non-toxic material may be used.

The sensing-contacts may be micro-circuit or nano-circuit sensors which are able to measure electrical currents generated through the circuits in response to an imposed voltage signal and/or reduction/oxidation reactions of chemical species at the circuit. Such circuits are known in the electrical arts and are produced using microlithography.

The sensing-contact may also be an optical sensor which is able to determine the concentrations of substances, chemical changes or cerebral blood flow rates. Optical sensors are preferably positioned at the tip of the depth electrode so that the exposed optical sensor projects from the electrode without increasing the diameter or thickness of the implanted device.

In the preferred embodiment utilizing the Peltier cooler the sensing-contacts are preferably located on the same probe as the temperature-contact. This construction allows for efficient implantation and removal if necessary due to unanticipated problems in the patient.

When using a Peltier cooler, the sensing-contacts are connected to sensing circuitry so that, upon detection of a physiological symptom of an incipient seizure, the sensing circuitry activates the supply of current to the heat-transfer operator and heat transfer is started, enabling the cooling of the targeted portion and suppression of the movement disorder episode. The sensing-contacts are preferably connected to the sensing circuitry through the distal end of the probe. The connection between the sensing-contacts and the sensing circuitry preferably runs alongside the Peltier cooler circuit or loop in order to minimize invasiveness.

In the preferred embodiment utilizing the thermal-electric cooler the sensing-contacts do not need to be located on a probe. Instead the sensing-contacts could be located on the face of the cold junction of the thermal-electric cooler or on the temperature contact itself. The invention also provides for the placement of the sensing-contacts on a probe of the depth-electrode or flat-electrode type. When using a depth-electrode type probe, the sensing-contacts are implanted into the brain. When using a flat-electrode type probe, the sensing-contacts are implanted beneath the skull on the surface of the brain.

When using a thermal-electric cooler, the sensing-contacts are connected to sensing circuitry so that, upon detection of a physiological symptom of an incipient seizure, the sensing circuitry activates the supply of current to the heat-transfer operator and heat transfer is started, enabling the cooling of the targeted portion and suppression of the movement disorder episode. The sensing-contacts can be connected to the sensing circuitry through the distal end of the probe, or simply around the exterior of the thermal-electric cooler if no probe is used. The connection between the sensing-contacts and the sensing circuitry preferably runs alongside the connection between the thermal-electric cooler and the power source in order to minimize invasiveness.

To provide for the automatic cessation of heat transfer in either embodiment, the sensing-contacts are able to signal the sensing circuitry to cease supply of power to the heat-transfer operator upon the achieving sufficient cooling. Sufficient cooling is achieved by the attainment of a predetermined temperature at the targeted portion, after heat transfer for a programmed period of time, after attainment of a predetermined temperature for a programmed period of time, after the subsidence of physiological symptoms or upon the sensing of physiological indications of the suppression of the movement disorder episode.

The period of time necessary for sufficient cooling may be programmed into the device, preferably into the sensing circuitry, before implantation or may be programmed by a physician, the patient or another person via telemetry or other remote means after implantation.

The temperature at the targeted portion may be determined by a thermocouple or other temperature detection means located near the targeted portion. The thermocouple or temperature detection means operates to measure the temperature of the targeted portion of the brain so that sufficient cooling may be ascertained or excessive cooling may be avoided. The thermocouple or temperature detection means is preferably located on the implanted probe or on the surface of the temperature-contact or cold junction of the thermal-electric cooler. The thermocouple or other temperature detection means is preferably connected to the sensing circuitry through the connection between the sensing-contacts and the sensing circuitry (sensing-contacts-sensing circuitry connection).

The sensing-contacts are powered by the power source through the connection between the sensing-contacts and the sensing circuitry (sensing-contact-sensing circuitry connection). The power source contains such sufficient energy that its replacement or recharging is not necessary for an extended period of time, perhaps as long as the patient's life, but at least about 3 years. The power source does not completely power off upon the sufficient cooling of the targeted portion. Rather, the power source continues to supply power to the sensing-contacts so that the sensing-contacts are able to detect the symptoms of the next movement disorder episode. The power source can be constructed so as to have a constant power component and a variable power component. The constant power component providing power to the sensing-contacts and the variable power component supplying a DC current to the heat-transfer operator to enable heat transfer.

The power source is preferably implanted in the patient away from the brain in a less sensitive area of the body. Such areas may be in the patient's axilla or abdomen, outside the skull, or in place of a portion of the skull which is removed. The power source is preferably enclosed in a titanium housing or other metal enclosure.

The titanium housing or metal enclosure can be used as an electrical ground for the electrical components of the device, such as the power source, sensing circuitry and heat-transfer operator. However, these electrical components may be otherwise grounded in the body. The titanium housing or metal enclosure can also be used as a heat sink or heat dissipater. The relatively large surface area of the housing and its location in a less heat-sensitive area of the body enable it to release heat efficiently.

In the embodiment of the invention utilizing manual activation of heat transfer the implantation of sensing-contacts and sensing-circuitry is not necessary. Rather, the power source can be turned on or activated by a person upon the sensing of physiological symptoms of a movement disorder episode. Because the power source does not need to supply power to sensing-contacts, the power source can be completely powered off between episodes.

The physiological symptoms are typically particular to the patient. Such symptoms can be the aura preceding an epileptic seizure. The aura is the period of time before the onset of a seizure when the patient experiences sensations or acts in a manner particular to an incipient seizure. Such sensations may be a stomach ache, photosensitivity or any other feeling which the patient recognizes as a precursor to a seizure. The patient may act in a way that others around them recognize as signaling an incipient seizure. These acts can include staring into space without reacting to the immediate surroundings or slowing down in speech or motion. In addition, an animal such as a dog may sense the incipient episode and react in a manner which is recognizable as being indicative of incipient episodes.

It is also provided that physiological symptoms on the patient's skin may be detected by a sensor worn by the patient. Upon detection of a symptom, the sensor is able to signal an alert, either audibly, through vibration or otherwise as is known in the art. The alert notifies the patient or another person to switch on the variable power source, or otherwise activate the transfer of heat away from the targeted portion. Such a sensor can be worn by the patient, for instance, on the inside of the patient's watchband. The sensor is preferably able to detect chemical changes on the skin's surface.

It is provided that upon identification of physiological symptoms of a movement disorder episode, the patient or another person may manually switch on the variable power source to activate heat transfer. The switching on process may include telemetry or other remote activation systems as are known in the art.

The manual embodiment is also able to utilize automatic cessation of heat transfer. Automatic cessation occurs upon reaching sufficient cooling of the targeted area. Sufficient cooling is achieved by the attainment of a predetermined temperature at the targeted portion or after heat transfer for a programmed period of time.

Finally, it is provided that the patient or another person may turn on the variable power source, or otherwise activate the heat transfer operator without the detection of a physiological symptom. Instead, such activation may be a prophylactic measure taken before the patient performs an activity during which an occurrence of a seizure would jeopardize the patient's safety. Such an activity may be driving a car or operating machinery. The heat transfer in such a situation would preferably occur for as long as the activity lasted to ensure that no movement disorder episodes occurred. Such prophylactic use may demand a great deal of energy and, therefore, may shorten the length of use of the power variable power source.

It is also contemplated that the heat-transfer operator may be another device or system which absorbs heat from a specific predetermined area. Such a device could include a housing containing a site for endothermic chemical reactions and connected to thermal conveyers such that the thermal conveyers transfer heat from their extremities, located at the targeted portion, to the site. Such heat transfer can be accomplished through convection of fluids or conduction. The thermal conveyer must be well-insulated to allow for effective heat transfer.

BRIEF DESCRIPTION OF THE DRAWINGS

FIGS. 2 and 2A are schematic representations of an implanted thermal transfer device constructed in accordance with the principles of the present invention and utilizing a Peltier cooler and optical sensing of symptoms with fiber optic circuitry.

FIGS. 3 and 3A are schematic representations of an implanted thermal transfer device constructed in accordance with the principles of the present invention and utilizing a Peltier cooler and electrical, electrochemical or chemical sensors with electrical circuitry and a thermocouple.

FIGS. 5, 5A and 5B are schematic representations of an implanted thermal transfer device constructed in accordance with the principles of the present invention and utilizing a thermal-electric cooler and optical sensing of symptoms with fiber optic circuitry.

FIGS. 6, 6A and 6B are schematic representations of an implanted thermal transfer device constructed in accordance with the principles of the present invention and utilizing a thermal-electric cooler and electrical, electrochemical or chemical sensors with electrical circuitry.

DETAILED DESCRIPTION OF PREFERRED EMBODIMENTS

Figures 1, 1A:
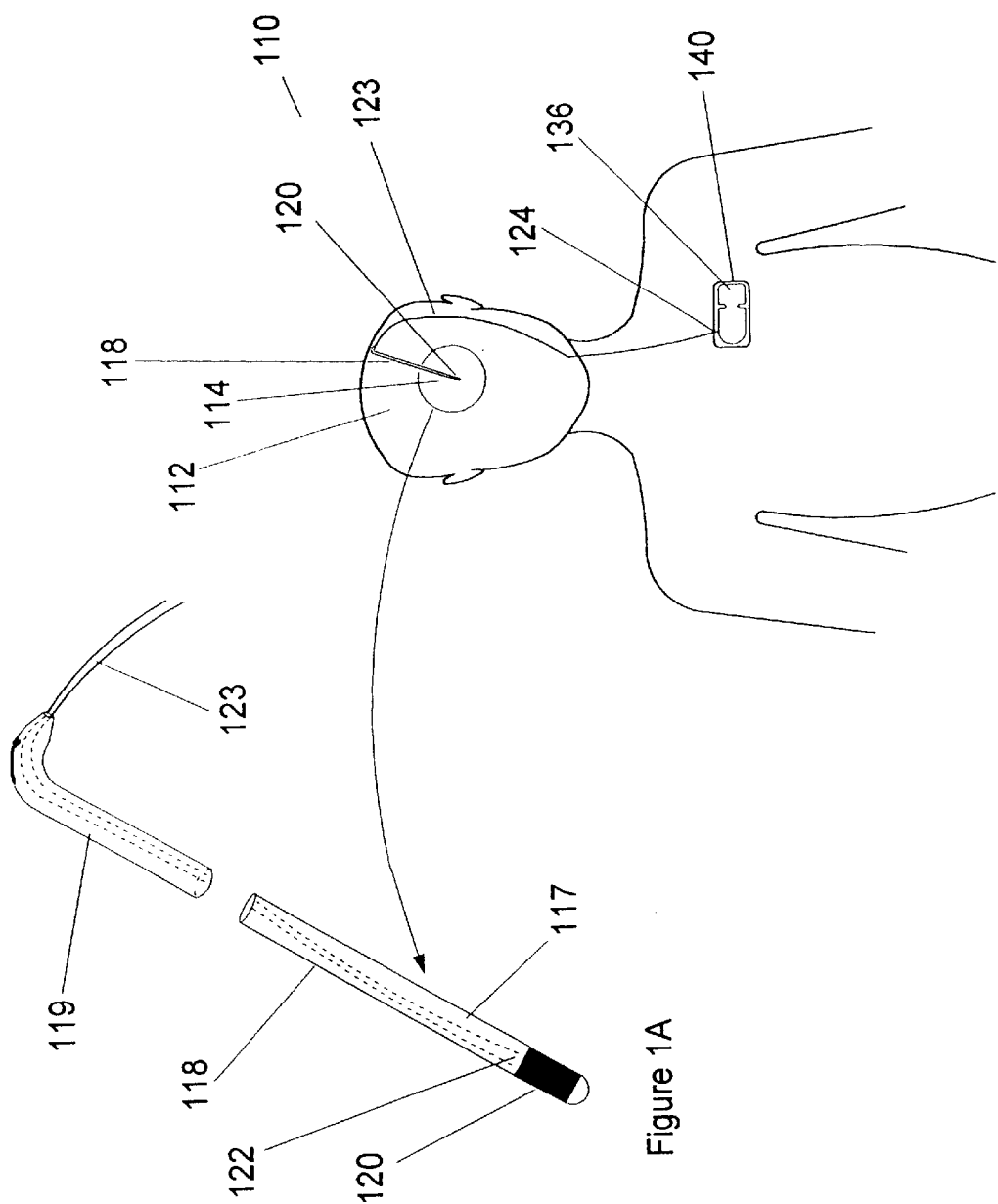
FIGS. 1 and 1A are schematic representations of an implanted thermal transfer device constructed in accordance with the principles of the present invention and utilizing a Peltier cooler and manual activation of heat transfer.

Referring to FIGS. 1 and 1A, details of the implanted thermal transfer device, utilizing a Peltier cooler and manual activation thereof, for treatment of movement disorder episodes will be set forth. The thermal transfer device 110 requires the positioning of a temperature-contact 120 at a targeted portion 114 in the brain 112. Temperature-contact 120 is located at the distal end 117 of a probe 118 and is preferably a gold or platinum collar as is known in the art. Probe 118 is inserted into brain 112 during implantation surgery. Probe 118 is preferably a flexible member with a thickness of about 5 millimeters or less.

The cold junction 122 of a Peltier cooler is thermally coupled to temperature-contact 120 so that it is capable of transferring heat away from temperature-contact 120 thus cooling targeted portion 114. Cold junction 122 and hot junction 124 are well-insulated so that heat is not absorbed from or by any tissue surrounding them. Peltier cooler circuit 123 preferably passes through the proximate end 119 of probe 118 and along the outside of the patient's skull through the patient's neck towards the patient's axilla until it reaches its hot junction 124. Hot junction 124 releases heat which is able to safely dissipate into the body. Such safe dissipation is facilitated by thermally coupling the hot junction 124 to housing 140 which is able to efficiently dissipate heat. Housing 140 is preferably a titanium enclosure.

Housing 140 is depicted as being mounted near the patient's axilla though it could be positioned farther from the brain in the patient's abdomen. Peltier cooler circuit 123 is connected to a power source 136 which provides an electric current to Peltier cooler circuit 123 when heat transfer is desired. Power source 136 typically comprises a long-lasting battery or other energy store and is preferably located within housing 140. The passage of the DC electric current through Peltier cooler circuit 123 results in the absorption of heat at cold junction 122, which results in absorption of heat by temperature-contact 120. Peltier cooler circuit 123 is preferably comprised of multiple pairs of dissimilar materials, preferably metals or semi-conducting materials, connected at cold junction 122 and hot junction 124.

Heat is transferred from cold junction 122 to hot junction 124 as long as an electric current passes through Peltier cooler circuit 123. When power source 136 ceases to provide power to Peltier cooler circuit 123, heat is no longer absorbed and the temperature of targeted portion 114 and temperature-contact 120 slowly return to normal body temperature.

Power source 136 is switched on or activated by the patient or another person in order to activate heat transfer. Power source 136 is switched on via telemetry or other remote methods. Typically, power source 136 is activated in response to the detection of a physiological symptom of an incipient movement disorder episode, though power source 136 can be activated as a prophylactic measure to prevent movement disorder episodes when the patient is particularly vulnerable to them or when their occurrence would endanger the patient.

The physiological symptoms may be detected by the patient, another person, or even by an animal, or most preferably by a sensor worn by the patient. The patient may recognize symptoms which coincide with the aura preceding the onset of a movement disorder episode. Typically during the aura the patient experiences sensations or acts in a particular manner which is indicative of an oncoming episode. The sensations may be a stomach ache, photosensitivity or any other feeling which the patient recognizes as a precursor to a seizure. The patient may recognize his own behavior as foretelling an oncoming episode or another person may identify such behavior. The behavior may include staring into space without reaction to the immediate surroundings, slowing down in speech or motion or other abnormal acts. An animal such as a dog may also sense oncoming episodes and alert the patient through its own particular behavior. Finally, a sensor worn on the patient's body may detect chemical changes on the patient's skin which are indicative of incipient episodes and alert the patient through a audible or vibrational alarm.

Power source 136 ceases to supply current to Peltier cooler circuit 123 when targeted portion 114 is sufficiently cooled. Sufficient cooling can be defined to occur when targeted portion 114 reaches a certain temperature or when heat transfer has occurred for a predetermined period of time. The predetermined period of time can be programmed before implantation, or after implantation via telemetry or other remote means, preferably by a physician.

Referring to FIGS. 2 and 2A, details of the implanted thermal transfer device, utilizing a Peltier cooler and automatic activation thereof, for treatment of movement disorder episodes will be set forth. The thermal transfer device 210 requires the positioning of a temperature-contact 220 at a targeted portion 214 in the brain 212. Temperature-contact 220 is located at the distal end 217 of a probe 218 and is preferably a gold or platinum collar as is known in the art. Probe 218 is inserted into brain 212 during implantation surgery. Probe 218 is preferably a flexible member with a thickness of about 5 millimeters or less.

Located at the tip of probe 218 is a sensing-contact which is an optical sensor 230. The optical sensor 230 is capable of measuring chemical changes, optical changes or cerebral blood flow changes. Optical sensor 230 may be coated with a material which is sensitive to the measured chemical conditions at the targeted portion 214 or optical sensor 230 may be polished such that it is sensitive to optical conditions or blood flow changes at the targeted portion 214.

Sensing-contact 230 is connected to sensing circuitry or controller 234 by sensing-contact-sensing circuitry connection 244 which is fiber optic. Sensing circuitry 234 is positioned in housing 240 which is a titanium enclosure. Sensing circuitry can be grounded to housing 240 or may be grounded elsewhere.

The cold junction 222 of a Peltier cooler is thermally coupled to temperature-contact 220 so that it is capable of transferring heat away from temperature-contact 220 thus cooling targeted portion 214. Cold junction 222 and hot junction 224 are well-insulated so that heat is not absorbed from or by any tissue surrounding them. Peltier cooler circuit 223 preferably passes through the proximate end 219 of probe 218 and along the outside of the patient's skull through the patient's neck towards the patient's axilla until it reaches its hot junction 224. Hot junction 224 releases heat which is able to safely dissipate into the body. Such safe dissipation is facilitated by thermally coupling the hot junction 224 to housing 240 which is able to efficiently dissipate heat. Housing 240 is preferably a titanium enclosure.

Housing 240 is depicted as being mounted near the patient's axilla though it could be positioned farther from the brain in the patient's abdomen. Peltier cooler circuit 223 is connected to a power source 236 which provides an electric current to Peltier cooler circuit 223 when heat transfer is desired. Power source 236 typically comprises a long-lasting battery or other energy store and is preferably located within housing 240. The passage of the DC electric current through Peltier cooler circuit 223 results in the absorption of heat at cold junction 222, which results in absorption of heat by temperature-contact 220. Peltier cooler circuit 223 is preferably comprised of multiple pairs of dissimilar materials, preferably metals or semi-conducting materials, connected at cold junction 222 and hot junction 224.

Heat is transferred from cold junction 222 to hot junction 224 as long as an electric current passes through Peltier cooler circuit 223. When power source 236 ceases to provide power to Peltier cooler circuit 223, heat is no longer absorbed and the temperature of targeted portion 214 and temperature-contact 220 slowly return to normal body temperature.

Symptoms of incipient seizures are measured as either chemical, optical or cerebral blood flow changes in the brain by the sensing-contacts 230. Upon identification of such symptoms, sensing/activation circuitry 234 activates power source 236 to supply DC current to the Peltier cooler circuit 223. As DC current is passed through Peltier cooler circuit 223, cold junction 222 absorbs heat from temperature-contact 220 which, in turn, absorbs heat from targeted point 214. Heat is released from hot junction 224 into housing 240 where it safely dissipates into the body.

Such heat transfer can occur for a programmed period of time controlled by sensing/activation circuitry 234, until a predetermined temperature is reached in targeted portion 214 or until sensing-contacts 230 no longer detect symptoms or otherwise detect subsidence of the movement disorder episode.

Referring to FIGS. 3 and 3A, details of the implanted thermal transfer device, utilizing a Peltier cooler and automatic activation thereof, for treatment of movement disorder episodes will be set forth. The thermal transfer device 310 requires the positioning of a temperature-contact 320 at a targeted portion 314 in the brain 312. Temperature-contact 320 is located at the distal end 317 of a probe 318 and is preferably a gold or platinum collar as is known in the art. Probe 318 is inserted into brain 312 during implantation surgery. Probe 318 is preferably a flexible member with a thickness of about 5 millimeters or less.

Located on the distal end 317 of probe 318 is at least one sensing-contact 330 which may be a gold or platinum contact capable of measuring electrical or electrochemical changes or may be micro-circuits or nano-circuits capable of measuring electrochemical or chemical changes. Such micro- or nano-circuits are known in the art of electrical circuitry and are typically fabricated using microlithography such that they are able to measure electrochemical or chemical changes at the level of neurons.

Sensing-contact 330 is connected to sensing circuitry or controller 334 by sensing-contact-sensing circuitry connection 344. Sensing circuitry 334 is positioned in housing 340 which is a titanium enclosure. Sensing circuitry can be grounded to housing 340 or may be grounded elsewhere.

The cold junction 322 of a Peltier cooler is thermally coupled to temperature-contact 320 so that it is capable of transferring heat away from temperature-contact 320 thus cooling targeted portion 314. Cold junction 322 and hot junction 324 are well-insulated so that heat is not absorbed from or by any tissue surrounding them. Peltier cooler circuit 323 preferably passes through the proximate end 319 of probe 318 and along the outside of the patient's skull through the patient's neck towards the patient's axilla until it reaches its hot junction 324. Hot junction 324 releases heat which is able to safely dissipate into the body. Such safe dissipation is facilitated by thermally coupling the hot junction 324 to housing 340 which is able to efficiently dissipate heat. Housing 340 is preferably a titanium enclosure.

Housing 340 is depicted as being mounted near the patient's axilla though it could be positioned farther from the brain in the patient's abdomen. Peltier cooler circuit 323 is connected to a power source 336 which provides an electric current to Peltier cooler circuit 323 when heat transfer is desired. Power source 336 typically comprises a long-lasting battery or other energy store and is preferably located within housing 340. The passage of the DC electric current through Peltier cooler circuit 323 results in the absorption of heat at cold junction 322, which results in absorption of heat by temperature-contact 320. Peltier cooler circuit 323 is preferably comprised of multiple pairs of dissimilar materials, preferably metals or semi-conducting materials, connected at cold junction 322 and hot junction 324.

Heat is transferred from cold junction 322 to hot junction 324 as long as an electric current passes through Peltier cooler circuit 323. When power source 336 ceases to provide power to Peltier cooler circuit 323, heat is no longer absorbed and the temperature of targeted portion 314 and temperature-contact 320 slowly return to normal body temperature.

Symptoms of incipient seizures are measured as either electrical, electrochemical or chemical changes in the brain by the sensing-contacts 330. Upon identification of such symptoms, sensing/activation circuitry 334 activates power source 336 to supply DC current to the Peltier cooler circuit 323. As DC current is passed through Peltier cooler circuit 323, cold junction 322 absorbs heat from temperature-contact 320 which, in turn, absorbs heat from targeted point 314. Heat is released from hot junction 324 into housing 340 where it safely dissipates into the body.

Such heat transfer can occur for a programmed period of time controlled by sensing/activation circuitry 334, until a predetermined temperature is reached in targeted portion 314 or until sensing-contacts 330 no longer detect symptoms or otherwise detect subsidence of the movement disorder episode.

The temperature at targeted portion 314 can be measured by thermocouple or other temperature detection device 316. Thermocouple 316 can be positioned on probe 318 and is connected to sensing-contact-sensing circuitry connection 344 such that the temperature at targeted portion 314 can be analyzed by circuitry 334.

Figures 4, 4A, 4B:
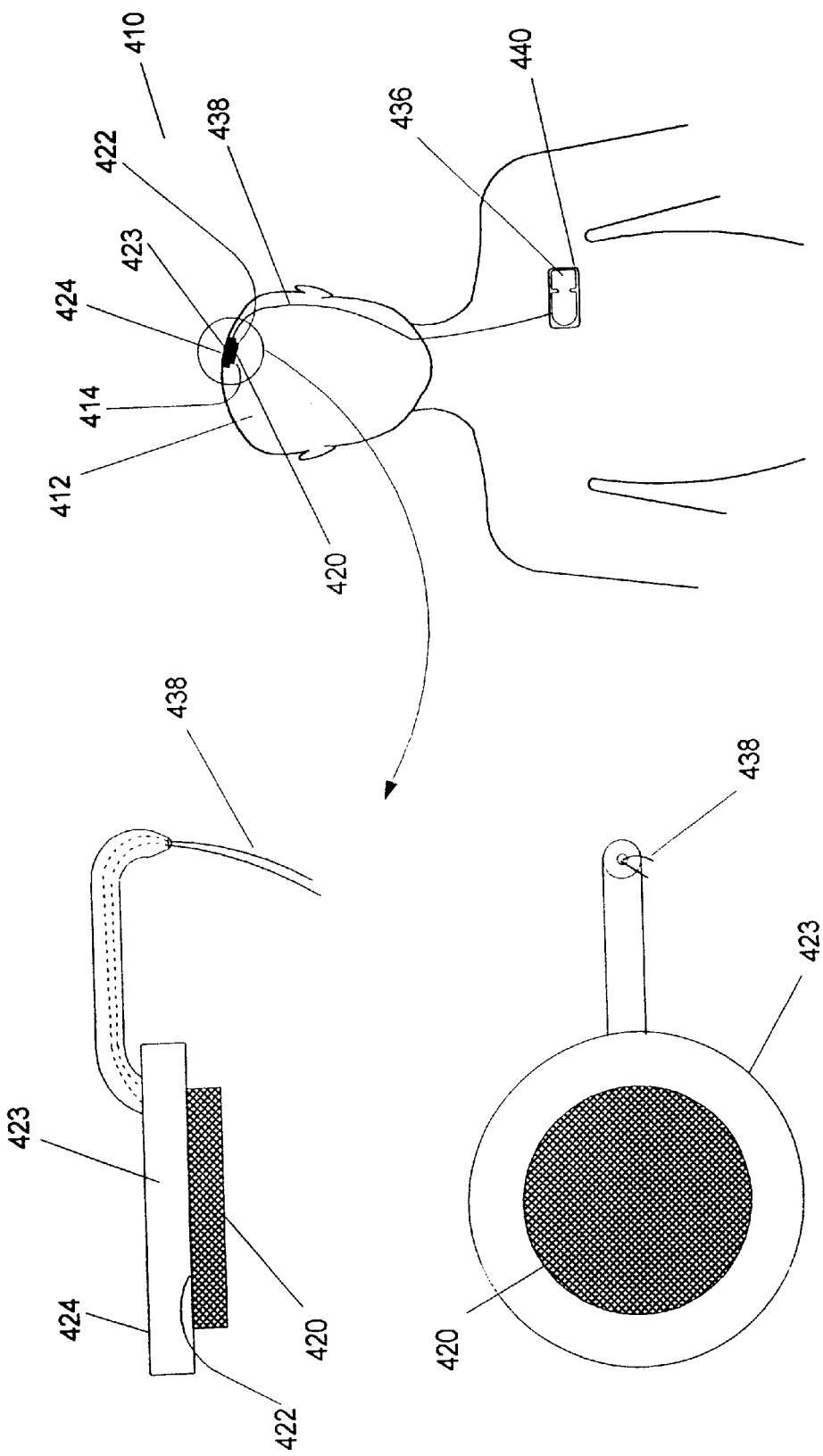
FIGS. 4, 4A and 4B are schematic representations of an implanted thermal transfer device constructed in accordance with the principles of the present invention and utilizing a thermal-electric cooler and manual activation of heat transfer.

Referring to FIGS. 4, 4A and 4B, details of the implanted thermal transfer device, utilizing a thermal-electric cooler and manual activation thereof, for treatment of movement disorder episodes will be set forth. The thermal transfer device 410 requires the positioning of a temperature-contact 420 at a targeted portion 414 on the brain 412. Temperature-contact 420 is located on the face of cold junction 422 or thermal-electric junction 423 and is preferably a gold or platinum foil or collar. Temperature-contact 420 and thermal-electric junction 423 are positioned at targeted portion 414 during implantation surgery. During implantation it is preferred that a piece of skull roughly equivalent in size to the thermal-electric junction 423 is removed and the temperature contact 420 and thermal-electric junction 423 are implanted in the resulting void.

Cold junction 422 is thermally coupled to temperature-contact 420 so that it is capable of transferring heat away from temperature-contact 420 thus cooling targeted portion 414. Hot junction 424 of thermal-electric cooler 423 faces away from the brain and is able to release heat which passes out of the head and dissipates into the atmosphere. Power source 436 is implanted in the patient's torso. Thermal-electric cooler 423 is connected to power source 436 via thermal-electric cooler-power source connection 438 such that a DC current supplied by power source 436 is able to pass through thermal-electric cooler 423 and cause cold junction 422 to absorb heat from temperature-contact 420 which, in turn, absorbs heat from targeted portion 414.

Thermal-electric cooler-power source connection 438 preferably passes along the outside of the patient's skull through the patient's neck towards the patient's axilla until it reaches power source 436. Power source 436 is preferably located inside housing 440. Housing 440 is preferably a titanium enclosure. Housing 440 is depicted as being mounted near the patient's axilla though it could be positioned farther from the brain in the patient's abdomen.

Power source 436 typically comprises a long-lasting battery or other energy store and is preferably located within housing 440. The passage of the DC electric current through thermal-electric cooler 423 results in the absorption of heat at cold junction 422, which results in absorption of heat by temperature-contact 420. Thermal-electric cooler 423 is preferably comprised of multiple semiconducting materials connected in series and is preferably enclosed by a sealed nontoxic enclosure.

Heat is transferred from cold junction 422 to hot junction 424 as long as an electric current passes through thermal-electric cooler 423. When power source 436 ceases to provide power to thermal-electric cooler 423, heat is no longer absorbed and the temperature of targeted portion 414 and temperature-contact 420 slowly return to normal body temperature.

Power source 436 is switched on or activated by the patient or another person in order to activate heat transfer. Power source 436 is switched on via telemetry or other remote methods. Typically, power source 436 is activated in response to the detection of a physiological symptom of an incipient movement disorder episode, though power source 436 can be activated as a prophylactic measure to prevent movement disorder episodes when the patient is particularly vulnerable to them or when their occurrence would endanger the patient.

The physiological symptoms may be detected by the patient, another person, or even by an animal, or most preferably by a sensor worn by the patient. The patient may recognize symptoms which coincide with the aura preceding the onset of a movement disorder episode. Typically during the aura the patient experiences sensations or acts in a particular manner which is indicative of an oncoming episode. The sensations may be a stomach ache, photosensitivity or any other feeling which the patient recognizes as a precursor to a seizure. The patient may recognize his own behavior as foretelling an oncoming episode or another person may identify such behavior. The behavior may include staring into space without reaction to the immediate surroundings, slowing down in speech or motion or other abnormal acts. An animal such as a dog may also sense oncoming episodes and alert the patient through its own particular behavior. Finally, a sensor worn on the patient's body may detect chemical changes on the patient's skin which are indicative of incipient episodes and alert the patient through a audible or vibrational alarm.

Power source 436 ceases to supply current to thermal-electric cooler 423 when targeted portion 414 is sufficiently cooled. Sufficient cooling can be defined to occur when targeted portion 414 reaches a certain temperature or when heat transfer has occurred for a predetermined period of time. The predetermined period of time can be programmed before implantation, or after implantation via telemetry or other remote means, preferably by a physician.

Referring to FIGS. 5, 5A and 5B, details of the implanted thermal transfer device, utilizing a thermal-electric cooler and automatic activation thereof, for treatment of movement disorder episodes will be set forth. The thermal transfer device 510 requires the positioning of a temperature-contact 520 at a targeted portion 514 on the brain 512. Temperature-contact 520 is located on the face of cold junction 522 or thermal-electric junction 523 and is preferably a gold or platinum foil or collar. Temperature-contact 520 and thermal-electric junction 523 are positioned at targeted portion 514 during implantation surgery. During implantation it is preferred that a piece of skull roughly equivalent in size to the thermal-electric junction 523 is removed and the temperature contact 520 and thermal-electric junction 523 are implanted in the resulting void.

Probe 518 is inserted into brain 512 during implantation surgery. Probe 518 is preferably a flexible member with a thickness of about 5 millimeters or less.

Located at the tip of probe 518 is a sensing-contact which is an optical sensor 530. The optical sensor 530 is capable of measuring chemical changes, optical changes or cerebral blood flow changes. Optical sensor 530 is coated with a material which is sensitive to the measured conditions at the targeted portion 514.

Sensing-contact 530 is connected to sensing circuitry or controller 534 by sensing-contact-sensing circuitry connection 544 which is fiber optic. Sensing circuitry 534 is positioned in housing 540 which is a titanium enclosure. Sensing circuitry can be grounded to housing 540 or may be grounded elsewhere.

Cold junction 522 is thermally coupled to temperature-contact 520 so that it is capable of transferring heat away from temperature-contact 520 thus cooling targeted portion 514. Hot junction 524 of thermal-electric cooler 523 faces away from the brain and is able to release heat which passes out of the head and dissipates into the atmosphere. Power source 536 is implanted in the patient's torso. Thermal-electric cooler 523 is connected to power source 536 via thermal-electric cooler-power source connection 538 such that a DC current supplied by power source 536 is able to pass through thermal-electric cooler 523 and cause cold junction 522 to absorb heat from temperature-contact 520 which, in turn, absorbs heat from targeted portion 514.

Thermal-electric cooler-power source connection 538 preferably passes along the outside of the patient's skull through the patient's neck towards the patient's axilla until it reaches power source 536. Power source 536 is preferably located inside housing 540. Housing 540 is preferably a titanium enclosure. Housing 540 is depicted as being mounted near the patient's axilla though it could be positioned farther from the brain in the patient's abdomen.

Power source 536 typically comprises a long-lasting battery or other energy store and is preferably located within housing 540. The passage of the DC electric current through thermal-electric cooler 523 results in the absorption of heat at cold junction 522, which results in absorption of heat by temperature-contact 520. Thermal-electric cooler 523 is preferably comprised of multiple semiconducting materials connected in series and is preferably enclosed by a sealed nontoxic enclosure.

Heat is transferred from cold junction 522 to hot junction 524 as long as an electric current passes through thermal-electric cooler 523. When power source 536 ceases to provide power to thermal-electric cooler 523, heat is no longer absorbed and the temperature of targeted portion 514 and temperature-contact 520 slowly return to normal body temperature.

Symptoms of incipient seizures are measured as either chemical, optical or cerebral blood flow changes in the brain by the sensing-contacts 530. Upon identification of such symptoms, sensing/activation circuitry 534 activates power source 536 to supply DC current to the thermal-electric junction 523. As DC current is passed through thermal-electric junction 523, cold junction 522 absorbs heat from temperature-contact 520 which, in turn, absorbs heat from targeted point 514. Heat is released from hot junction 524 into housing 540 where it safely dissipates into the body.

Such heat transfer can occur for a programmed period of time controlled by sensing/activation circuitry 534, until a predetermined temperature is reached in targeted portion 514 or until sensing-contacts 530 no longer detect symptoms or otherwise detect subsidence of the movement disorder episode.

Referring to FIGS. 6, 6A and 6B, details of the implanted thermal transfer device, utilizing a thermal-electric cooler and automatic activation thereof, for treatment of movement disorder episodes will be set forth. The thermal transfer device 610 requires the positioning of a temperature-contact 620 at a targeted portion 614 on the brain 612. Temperature-contact 620 is located on the face of cold junction 622 or thermal-electric junction 623 and is preferably a gold or platinum foil or collar. Temperature-contact 620 and thermal-electric junction 623 are positioned at targeted portion 614 during implantation surgery. During implantation it is preferred that a piece of skull roughly equivalent in size to the thermal-electric junction 623 is removed and the temperature contact 620 and thermal-electric junction 623 are implanted in the resulting void.

Located on the face of temperature-contact 620 or thermal-electric cooler 623 is a sensing-contact 630. Sensing-contact 630 is capable of measuring electrical, electrochemical or chemical changes.

Sensing-contact 630 is connected to sensing circuitry or controller 634 by sensing-contact-sensing circuitry connection 644. Sensing circuitry 634 is positioned in housing 640 which is a titanium enclosure. Sensing circuitry can be grounded to housing 640 or may be grounded elsewhere.

Cold junction 622 is thermally coupled to temperature-contact 620 so that it is capable of transferring heat away from temperature-contact 620 thus cooling targeted portion 614. Hot junction 624 of thermal-electric cooler 623 faces away from the brain and is able to release heat which passes out of the head and dissipates into the atmosphere. Power source 636 is implanted in the patient's torso. Thermal-electric cooler 623 is connected to power source 636 via thermal-electric cooler-power source connection 638 such that a DC current supplied by power source 636 is able to pass through thermal-electric cooler 623 and cause cold junction 622 to absorb heat from temperature-contact 620 which, in turn, absorbs heat from targeted portion 614.

Thermal-electric cooler-power source connection 638 preferably passes along the outside of the patient's skull through the patient's neck towards the patient's axilla until it reaches power source 636. Power source 636 is preferably located inside housing 640. Housing 640 is preferably a titanium enclosure. Housing 640 is depicted as being mounted near the patient's axilla though it could be positioned farther from the brain in the patient's abdomen.

Power source 636 typically comprises a long-lasting battery or other energy store and is preferably located within housing 640. The passage of the DC electric current through thermal-electric cooler 623 results in the absorption of heat at cold junction 622, which results in absorption of heat by temperature-contact 620. Thermal-electric cooler 623 is preferably comprised of multiple semiconducting materials connected in series and is preferably enclosed by a sealed nontoxic enclosure.

Heat is transferred from cold junction 622 to hot junction 624 as long as an electric current passes through thermal-electric cooler 623. When power source 636 ceases to provide power to thermal-electric cooler 623, heat is no longer absorbed and the temperature of targeted portion 614 and temperature-contact 620 slowly return to normal body temperature.

Symptoms of incipient seizures are measured as either electrical, electrochemical or chemical changes in the brain by the sensing-contacts 630. Upon identification of such symptoms, sensing circuitry 634 activates power source 636 to supply DC current to the thermal-electric junction 623. As DC current is passed through thermal-electric junction 623, cold junction 622 absorbs heat from temperature-contact 620 which, in turn, absorbs heat from targeted point 614. Heat is released from hot junction 624 into housing 640 where it safely dissipates into the body.

Such heat transfer can occur for a programmed period of time controlled by sensing/activation circuitry 634, until a predetermined temperature is reached in targeted portion 614 or until sensing-contacts 630 no longer detect symptoms or otherwise detect subsidence of the movement disorder episode

EXAMPLE 1

Probe 118 of the depth electrode type is implanted in the patient's brain 112 so that temperature-contact 120 is located at targeted portion 114. A pair of dissimilar conductors in a Peltier cooler 123 are positioned such that one junction is located adjacent to temperature-contact 120 and another junction is located next to housing 140. Housing 140 is implanted in the patient's torso and is preferably a titanium enclosure. Power source 136 is positioned in housing 140. Power source 136 is connected to pair of dissimilar conductors in a Peltier cooler 123 such that a DC current can be passed through the Peltier cooler circuit 123. The DC current travels in a certain direction such that cold junction of Peltier cooler 122 is positioned next to temperature-contact 120 and hot junction of Peltier cooler 124 is positioned near housing 140.

The Peltier cooler circuit is thermally coupled to temperature contact 120 and housing 140 such that heat is transferred from temperature-contact 120 to cold junction 122 and from hot junction 124 to housing 140 upon operation of the Peltier cooler.

When physiological symptoms of incipient seizures are identified or recognized by the patient, another person or an animal, a person remotely activates power source 136 to supply DC current to the Peltier cooler circuit 123. As DC current is passed through Peltier cooler circuit 123, cold junction 122 absorbs heat from temperature-contact 120 which, in turn, absorbs heat from targeted portion 114. Heat is released from hot junction 124 into housing 140 where it safely dissipates into the body.

Such heat transfer can occur for a programmed period of time, until a predetermined temperature is reached in targeted portion 114 or until the patient no longer detects symptoms or otherwise detects subsidence of the movement disorder episode. Heat transfer may be automatically discontinued or turned off by the patient or another person.

EXAMPLE 2

Probe 218 of the depth electrode type is implanted in the patient's brain 212 so that temperature-contact 220 is located at targeted portion 214. Located at the tip of probe 218 is at least one sensing-contact 230 which is an optical sensor capable of measuring chemical, optical or cerebral blood flow changes. As is known in the art, such optical sensors may be coated with a material which is sensitive to the surrounding chemical conditions undergoing sensing. Chemical, optical or cerebral blood flow changes in the targeted portion 214 of the brain 212 are sensed through changes in optics within the optical sensor.

Sensing-contact 230 is connected to sensing/activation circuitry 234 by sensing-contact-circuitry connection 244. Sensing-contact-circuitry connection 244 is a fiber optic which is able to transmit data in an optical form to sensing/activation circuitry 234. Sensing/activation circuitry 234 is positioned in housing 240 which provides a secure housing for the circuitry 234. Circuitry 234 can be grounded to housing 240. Housing 240 is implanted in the patient's torso, preferably in the patient's axilla.

Power source 236 supplies power to enable sensing through the sensing/activation circuitry 234. Power source 236 is positioned in housing 240. Power source 236 is further connected to the Peltier cooler such that a DC current can be passed through the Peltier cooler circuit 223. The DC current travels in a certain direction such that cold junction of Peltier cooler 222 is positioned next to temperature-contact 220 and hot junction of Peltier cooler 224 is positioned next to housing 240.

The Peltier cooler circuit is thermally coupled to temperature contact 220 and housing 240 such that heat is transferred from temperature-contact 220 to cold junction 222 and from hot junction 224 to housing 240.

Symptoms of incipient seizures are measured as either chemical, optical or cerebral blood flow changes in the brain by the sensing-contacts 230. Upon identification of such symptoms, sensing/activation circuitry 234 activates power source 236 to supply DC current to the Peltier cooler circuit 223. As DC current is passed through Peltier cooler circuit 223, cold junction 222 absorbs heat from temperature-contact 220 which, in turn, absorbs heat from targeted point 214. Heat is released from hot junction 224 into housing 240 where it safely dissipates into the body.

Such heat transfer can occur for a programmed period of time controlled by sensing/activation circuitry 234, until a predetermined temperature is reached in targeted portion 214 or until sensing-contacts 230 no longer detect symptoms or otherwise detect subsidence of the movement disorder episode.

EXAMPLE 3

Probe 318 of the depth electrode type is implanted in the patient's brain 312 so that temperature-contact 320 is located at targeted portion 314. Also located on probe 318 are sensing-contacts 330 which may be gold or platinum contacts capable of measuring electrical or electrochemical changes or may be micro-circuits or nano-circuits capable of measuring electrochemical or chemical changes. Such micro- or nano-circuits are known in the art of electrical circuitry and are typically fabricated using microlithography such that they are able to measure electrochemical or chemical changes at the level of neurons.

Sensing-contacts 330 are connected to sensing/activation circuitry 334 by sensing-contact-circuitry connection 344. Sensing/activation circuitry 334 is positioned in housing 340 which provides a secure housing for the circuitry 334. Circuitry 334 can be grounded to housing 340. Housing 340 is implanted in the patient's torso, preferably in the patient's axilla.

Power source 336 supplies power to sensing-contacts 330 through the sensing/activation circuitry 334. Power source 336 is positioned in housing 340. Power source 336 is further connected to the Peltier cooler such that a DC current can be passed through the Peltier cooler circuit 323. The DC current travels in a certain direction such that cold junction of Peltier cooler 322 is positioned next to temperature-contact 320 and hot junction of Peltier cooler 324 is positioned next to housing 340.

The Peltier cooler circuit is thermally coupled to temperature contact 320 and housing 340 such that heat is transferred from temperature-contact 320 to cold junction 322 and from hot junction 324 to housing 340.

Symptoms of incipient seizures are measured as either electrical, electrochemical and/or chemical changes in the brain by the sensing-contacts 330. Upon identification of such symptoms, sensing/activation circuitry 334 activates power source 336 to supply DC current to the Peltier cooler circuit 323. As DC current is passed through Peltier cooler circuit 323, cold junction 322 absorbs heat from temperature-contact 320 which, in turn, absorbs heat from targeted point 314. Heat is released from hot junction 324 into housing 340 where it safely dissipates into the body.

Such heat transfer can occur for a programmed period of time controlled by sensing/activation circuitry 334, until a predetermined temperature is reached in targeted portion 314 or until sensing-contacts 330 no longer detect symptoms or otherwise detect subsidence of the movement disorder episode. The temperature at targeted portion 314 is measured by thermocouple 316. Thermocouple 316 is positioned on probe 318 and is connected to sensing-contact-sensing circuitry connection 344 such that the temperature at targeted portion 314 can be analyzed by circuitry 334.

EXAMPLE 4

A piece of skull is removed and thermal-electric cooler 423 is implanted in its place such that cold junction 422 of thermal-electric cooler 423 is adjacent to the surface of the brain 412. Hot junction 424 of thermal-electric cooler 423 faces away from the brain. Thermal-electric cooler 423 is connected to power source 436 via thermal-electric cooler-power source connection 438 such that a DC current supplied by power source 436 is able to pass through thermal-electric cooler 423 and cause cold junction 422 to absorb heat from temperature-contact 420 which, in turn, absorbs heat from targeted portion 414. Heat can be released from hot junction 424 and pass out of the head dissipating into the atmosphere. Power source 436 is implanted in the patient's torso.

When physiological symptoms of incipient seizures are identified or recognized by the patient, another person or an animal, a person remotely activates power source 436 to supply DC current to thermal-electric cooler 423. As DC current is passed through thermal-electric cooler 423, cold junction 422 absorbs heat from temperature-contact 420 which, in turn, absorbs heat from targeted portion 414. Heat is released from hot junction 424 where it safely dissipates into the atmosphere.

Such heat transfer can occur for a programmed period of time, until a predetermined temperature is reached in targeted portion 414 or until the patient no longer detects symptoms or otherwise detects subsidence of the movement disorder episode. Heat transfer may be automatically discontinued or turned off by the patient or another person.

EXAMPLE 5

A piece of skull is removed and thermal-electric cooler 523 is implanted in its place such that cold junction 522 of thermal-electric cooler 523 is adjacent to the surface of the brain 512. Hot junction 524 of thermal-electric cooler 523 faces away from the brain. Thermal-electric cooler 523 is connected to power source 536 via thermal-electric cooler-power source connection 538 such that a DC current supplied by power source 536 is able to pass through thermal-electric cooler 523 and cause cold junction 522 to absorb heat from temperature-contact 520 which, in turn, absorbs heat from targeted portion 514. Heat can be released from hot junction 524 and pass out of the head dissipating into the atmosphere. Power source 536 is implanted in the patient's torso.

Probe 518 of the depth electrode type is implanted in the patient's brain 512. Located at the tip of probe 518 is at least one sensing-contact 530 which is an optical sensor capable of measuring chemical, optical or cerebral blood flow changes. As is known in the art, such optical sensors are typically coated with a material which is sensitive to the surrounding conditions undergoing sensing. Chemical, optical or cerebral blood flow changes in the targeted portion 514 of the brain 512 are sensed through changes in optics within the optical sensor.

Sensing-contact 530 is connected to sensing/activation circuitry 534 by sensing-contact-circuitry connection 544. Sensing-contact-circuitry connection 544 is a fiber optic which is able to transmit data in an optical form to sensing/activation circuitry 534. Sensing/activation circuitry 534 is positioned in housing 540 which provides a secure housing for the circuitry 534. Circuitry 534 can be grounded to housing 540. Housing 540 is implanted in the patient's torso, preferably in the patient's axilla. Power source 536 supplies power to enable sensing through the sensing/activation circuitry 534.

Symptoms of incipient seizures are measured as either chemical, optical or cerebral blood flow changes in the brain by the sensing-contacts 530. Upon identification of such symptoms, sensing/activation circuitry 534 activates power source 536 to supply DC current to the thermal-electric cooler 523. As DC current is passed through thermal-electric cooler 523, cold junction 522 absorbs heat from temperature-contact 520 which, in turn, absorbs heat from targeted point 514. Heat is released from hot junction 524 into housing 540 where it safely dissipates into the body.

Such heat transfer can occur for a programmed period of time controlled by sensing/activation circuitry 534, until a predetermined temperature is reached in targeted portion 514 or until sensing-contacts 530 no longer detect symptoms or otherwise detect subsidence of the movement disorder episode.

EXAMPLE 6

A piece of skull is removed and thermal-electric cooler 623 is implanted in its place such that cold junction 622 of thermal-electric cooler 623 is adjacent to the surface of the brain 612. Hot junction 624 of thermal-electric cooler 623 faces away from the brain. Thermal-electric cooler 623 is connected to power source 636 via thermal-electric cooler-power source connection 638 such that a DC current supplied by power source 636 is able to pass through thermal-electric cooler 623 and cause cold junction 622 to absorb heat from temperature-contact 620 which, in turn, absorbs heat from targeted portion 614. Heat can be released from hot junction 624 and pass out of the head dissipating into the atmosphere. Power source 636 is implanted in the patient's torso.

Located on the face of temperature-contact 620 or thermal-electric cooler 623 is at least one sensing-contact 630 capable of measuring electrical, electrochemical or chemical changes. Sensing-contact 630 is connected to sensing/activation circuitry 634 by sensing-contact-circuitry connection 644. Sensing-contact-circuitry connection 644. Sensing/activation circuitry 634 is positioned in housing 640 which provides a secure housing for the circuitry 634. Circuitry 634 can be grounded to housing 640. Housing 640 is implanted in the patient's torso, preferably in the patient's axilla. Power source 636 supplies power to enable sensing through the sensing/activation circuitry 634.

Symptoms of incipient seizures are measured as either electrical, electrochemical or chemical changes in the brain by the sensing-contacts 630. Upon identification of such symptoms, sensing/activation circuitry 634 activates power source 636 to supply DC current to the thermal-electric cooler 623. As DC current is passed through thermal-electric cooler 623, cold junction 622 absorbs heat from temperature-contact 620 which, in turn, absorbs heat from targeted point 614. Heat is released from hot junction 624 into housing 640 where it safely dissipates into the body.

Such heat transfer can occur for a programmed period of time controlled by sensing/activation circuitry 634, until a predetermined temperature is reached in targeted portion 614 or until sensing-contacts 630 no longer detect symptoms or otherwise detect subsidence of the movement disorder episode.

What is claimed is:

1. A method of suppressing seizures in a patient comprising:
   detecting with at least one fiber optic sensing-contact positioned in the brain a physiological symptom associated with a seizure; and
   in response to detection of the symptom, automatically activating a heat-transfer operator to selectively transfer heat away from a targeted portion in the brain previously identified as being related to seizures in the patient by absorbing heat into a temperature-contact situated at the targeted portion and thermally coupled to the heat-transfer operator.

2. The method of claim 1 wherein the symptom is an electrical change within the brain.

3. The method of claim 1 wherein the symptom is a chemical change within the brain.

4. The method of claim 1 wherein the symptom is an electrochemical change within the brain.

5. The method of claim 1 wherein the sensing-contact comprises at least one macro-sensing-contact.

6. The method of claim 1 wherein the sensing-contact comprises at least one micro-sensing-contact.

7. The method of claim 1 wherein the sensing-contact comprises at least one nano-sensing-contact.

8. The method of claim 1 wherein the sensing-contact and the temperature-contact are located on a distal end of a probe.

9. The method of claim 1 wherein the sensing-contact is powered by a power source, the power source supplying power to activate the heat-transfer operator upon the detection of a symptom.

10. The method of claim 9 wherein the power source stores sufficient energy to suppress seizures in a patient for an extended period of time.

11. The method of claim 9 wherein the variable power source automatically ceases to supply power to the heat-transfer operator after the targeted portion is sufficiently cooled.

12. The method of claim 11 wherein the targeted portion is sufficiently cooled when there is a subsidence of the physiological symptom, the subsidence detected by the sensing-contact.

13. The method of claim 11 wherein the targeted portion is sufficiently cooled when the targeted portion reaches a predetermined temperature.

14. The method of claim 13 wherein a thermocouple measures the temperature at the targeted portion.

15. The method of claim 11 wherein the targeted portion is sufficiently cooled when heat is transferred away from the targeted portion for a programmed period of time.

16. The method of claim 15 wherein the period of time is programmed by a physician.

17. The method of claim 1 wherein the heat-transfer operator is activated by switching on a power source, the power source supplying power to the heat-transfer operator.

18. The method of claim 17 wherein the power source automatically ceases to supply power to the heat-transfer operator after the targeted portion is sufficiently cooled.

19. The method of claim 18 wherein the targeted portion is sufficiently cooled when a programmable period of time lapses.

20. The method of claim 18 wherein the targeted portion is sufficiently cooled when the targeted portion reaches a predetermined temperature.

21. The method of claim 1 wherein the heat-transfer operator is a Peltier cooler.

22. The method of claim 21 wherein the Peltier cooler is implanted in the patient's torso.

23. The method of claim 1 wherein the heat-transfer operator is a thermal-electric cooler.

24. The method of claim 23 wherein the thermal-electric cooler is implanted adjacent to the patient's skull.

25. The method of claim 1 wherein the targeted portion is a small point-like volume of the brain.

26. A method of allowing suppression of a movement disorder in a patient comprising:
   surgically implanting in the patient's brain at least one temperature-contact at a predetermined targeted portion;
   thermally coupling the temperature-contact to a Peltier cooler; and
   operating the heat-transfer operator to transfer heat away from the temperature-contact such that the targeted portion is cooled and the movement disorder is suppressed.

27. The method of claim 26 wherein the hot junction of the Peltier cooler is implanted outside of the patient's skull.

28. The method of claim 26 wherein the hot junction of the Peltier cooler is implanted in the patient's torso.

29. The method of claim 26 wherein a person activates operation of the Peltier cooler after sensing a physiological symptom of a movement disorder.

30. The method of claim 29 wherein the physiological symptom is the aura preceding an epileptic seizure.

31. The method of claim 30 wherein the patient is the person performing both the detecting and the activating.

32. The method of claim 29 wherein the person is the patient.

33. The method of claim 26 further comprising the steps of:
   surgically implanting in the patient's brain at least one sensing-contact for sensing a physiological symptom of a movement disorder; and
   connecting the sensing-contact to a power source which supplies power for the operation of the Peltier cooler upon the sensing of a symptom, the power source being surgically implanted in the patient's body.

34. The method of claim 33 wherein the sensing-contact and the temperature-contact are positioned on a probe.

35. The method of claim 26 further comprising surgically implanting in the patient's brain at least one sensing-contact for sensing a symptom of the movement disorder, the symptom being electrical changes in the brain.

36. The method of claim 26 further comprising surgically implanting in the patient's brain at least one sensing-contact for sensing a symptom of the movement disorder, the symptom being chemical changes in the brain.

37. The method of claim 26 further comprising surgically implanting in the patient's brain at least one sensing-contact for sensing a symptom of the movement disorder, the symptom being electrochemical changes in the brain.

38. A method of controlling or preventing seizures in a patient comprising:
sensing a symptom of an incipient seizure, the symptom being a chemical change within the brain; and
thereafter transferring heat away from a predetermined targeted portion in the brain by use of a heat-transfer operator implanted in the patient.

39. The method of claim 38 wherein at least one temperature-contact, located at the targeted portion and coupled to the heat-transfer operator, absorbs heat from the targeted portion.

40. The method of claim 39 wherein the heat-transfer operator is a Peltier cooler implanted in the patient's torso.

41. The method of claim 39 wherein the heat-transfer operator is a thermal-electric cooler implanted adjacent to the patient's skull.

42. The method of claim 39 wherein a person senses the symptom and activates the transfer of heat manually.

43. The method of claim 42 wherein the symptom is recognized by the patient as an aura.

44. The method of claim 38 wherein the transfer of heat automatically ceases after a predetermined period of time.

45. The method of claim 38 wherein a sensing-contact positioned in the brain senses the symptom and activates the transfer of heat automatically.

46. The method of claim 38 wherein the sensing-contact deactivates the transfer of heat after sensing a subsidence of the symptom.

47. The method of claim 38 wherein the sensing-contact deactivates the transfer of heat after a programmed period of time.

48. The method of claim 38 wherein the sensing-contact deactivates the transfer of heat when the targeted portion reaches a predetermined temperature.

49. An implanted seizure-suppressing device comprising:
at least one temperature-contact positioned at a targeted portion in the brain; and
a heat-transfer operator positioned away from the targeted portion and thermally coupled to the temperature-contact,
whereby heat is withdrawn from the targeted portion upon activation of the heat-transfer operator.

50. The device of claim 49 wherein the heat-transfer operator is a Peltier cooler implanted on the patient's skull.

51. The device of claim 49 wherein the heat-transfer operator is a thermal-electric cooler implanted in the patient's axilla.

52. The device of claim 49 further comprising a sensor which signals an alert upon sensing an incipient seizure so that the heat-transfer operator may be activated.

53. The device of claim 52 wherein the sensor senses changes on the surface of the patient's skin indicative of an incipient seizure.

54. The device of claim 53 wherein the sensor is worn by the patient.

55. The device of claim 49 further comprising a power source implanted in the patient, the power source supplying power to activate the heat-transfer operator.

56. The device of claim 55 wherein a person turns on the power source.

57. The device of claim 56 wherein the person is the patient.

58. The device of claim 56 wherein the person turns on the power source before the patient performs an activity during which an occurrence of a seizure would jeopardize the patient's safety.

59. The device of claim 56 wherein the person turns on the power source upon sensing an incipient seizure.

60. The device of claim 55 wherein the power source automatically ceases to supply power to the heat-transfer operator after heat has been sufficiently withdrawn from the targeted portion.

61. The device of claim 60 wherein heat has been sufficiently withdrawn from the targeted portion when a programmable period of time lapses.

62. The device of claim 60 wherein heat has been sufficiently withdrawn from the targeted portion when the targeted portion reaches a predetermined temperature.

63. The device of claim 55 further comprising at least one sensing-contact for detecting a physiological symptom of an incipient seizure, the sensing-contact implanted in the brain and powered by the power source.

64. The device of claim 63 wherein the sensing-contact senses electrical changes in the brain.

65. The device of claim 63 wherein the sensing-contact senses chemical changes in the brain.

66. The device of claim 63 wherein the sensing-contact senses electrochemical changes in the brain.

67. The device of claim 63 wherein the sensing-contact is connected to a controller, the controller activating the thermal-electric cooler upon detection of a symptom.

68. The device of claim 67 wherein the controller and power source are positioned in a can implanted in the patient's torso.

69. The device of claim 67 wherein the temperature-contact and the sensing-contact are located on a probe.

70. A method of suppressing seizures in a patient comprising:
detecting a physiological symptom associated with a seizure; and
in response to detection of the symptom, selectively transferring heat away from a targeted portion in the brain previously identified as being related to seizures in the patient by absorbing heat into a temperature-contact situated at the targeted portion and thermally coupled to a thermal conveyor, the thermal conveyor transferring heat from the temperature-contact through a thermal transfer fluid.

71. The method of claim 70 wherein the thermal conveyor transfers heat from the temperature-contact to the thermal transfer fluid by conduction through mechanical contact.

72. The method of claim 70 wherein the thermal conveyor transfers heat from the temperature-contact by conduction through a thermal transfer fluid.

73. The method of claim 70 wherein the thermal conveyor transfers heat from the temperature-contact by convection through a thermal transfer fluid.

74. The method of claim 70 wherein the thermal conveyor is thermally coupled to a reaction chamber, the reaction chamber providing a site for controlled endothermic chemical reactions.

75. A method of suppressing seizures in a patient comprising:
detecting with a sensing-contact positioned in the brain a physiological symptom associated with a seizure; and
in response to detection of the symptom, activating a heat-transfer operator to selectively transfer heat away from a targeted portion in the brain previously identified as being related to seizures in the patient by absorbing heat into a temperature-contact situated at the targeted portion and thermally coupled to the heat-transfer operator, the sensing-contact deactivating the transfer of heat after sensing a subsidence of the symptom.

76. A method of suppressing seizures in a patient comprising:

providing a probe having a distal end, the distal end having a sensing-contact and a temperature-contact, the temperature-contact adapted for thermal coupling to a heat-transfer operator;

positioning the distal end in the patient's brain such that the distal end is situated at a targeted portion in the brain previously identified as being related to seizures in the patient;

detecting with the sensing-contact a physiological symptom associated with a seizure; and in response to detection of the symptom, automatically activating the heat-transfer operator to selectively transfer heat away from the targeted portion by absorbing heat into the temperature-contact situated at the targeted portion.

77. The method of claim 76 wherein the sensing-contact is a fiber optic contact.

* * * * *